United States Patent [19]

Okazaki et al.

[11] Patent Number: 5,078,143
[45] Date of Patent: Jan. 7, 1992

[54] LITHOTRITY APPARATUS USING ULTRASONIC WAVES OR SHOCK WAVES FOR PREVENTING ERRONEOUS IRRADIATION OF ULTRASONIC WAVES OR SHOCK WAVES

[75] Inventors: Kiyoshi Okazaki, Takanezawa; Nobuyuki Iwama, Tokyo; Hirotsugu Suzuki, Ootawara, all of Japan

[73] Assignee: Kabushiki Kaisha Toshiba, Kawasaki, Japan

[21] Appl. No.: 504,304

[22] Filed: Apr. 4, 1990

[30] Foreign Application Priority Data

Apr. 7, 1989 [JP] Japan .................................. 1-88728
Sep. 8, 1989 [JP] Japan ................................. 1-233401

[51] Int. Cl.$^5$ .............................................. A61B 17/22
[52] U.S. Cl. ........................... 128/660.03; 128/24 AA; 128/24 EL; 128/804
[58] Field of Search ........ 128/24 EL, 24 AA, 660.03, 128/804

[56] References Cited

U.S. PATENT DOCUMENTS

| | | | |
|---|---|---|---|
| 4,617,931 | 10/1986 | Dory . | |
| 4,763,652 | 8/1988 | Brisson et al. | 128/24 EL |
| 4,803,995 | 2/1989 | Ishida et al. | 128/660.03 |
| 4,819,621 | 4/1989 | Ueberle et al. | 128/24 EL |
| 4,829,986 | 5/1989 | Eichler et al. | 128/24 EL |
| 4,834,074 | 5/1989 | Reichenberger | 128/24 EL |
| 4,940,050 | 7/1990 | Forssmann et al. | 128/24 EL |
| 4,958,639 | 9/1990 | Uchiyama et al. | 128/660.03 |

*Primary Examiner*—Ruth S. Smith
*Attorney, Agent, or Firm*—Finnegan, Henderson, Farabow, Garrett and Dunner

[57] ABSTRACT

A shock wave lithotrity apparatus comprises an applicator which includes a first transducer for generating ultrasonic waves and for converging the ultrasonic waves on a focal point to treat an object, a second transducer for generating ultrasonic waves at a low level for echography, and a water bag for transmitting the ultrasonic waves to the object. A lithotrity unit and a B-mode imaging unit are respectively connected to the first and second transducers. When a position mode is selected, the second transducer is driven by the B-mode imaging unit and the echography is displayed and the first transducer is driven by the lithotrity unit at a low voltage to detect the intensity of the echo signal. The degree of focus-calculus matching is calculated based on the intensity. The operator adjusts the position of the first transducer by referring to the echography and the matching degree. The operation of a trigger switch is disabled in order to inhibit the drive of the first transducer at a high level in the positioning mode. In a lithotrity mode the first transducer is driven at the high level in order to generate the shock wave at the focus point upon the operation of the trigger switch.

19 Claims, 7 Drawing Sheets

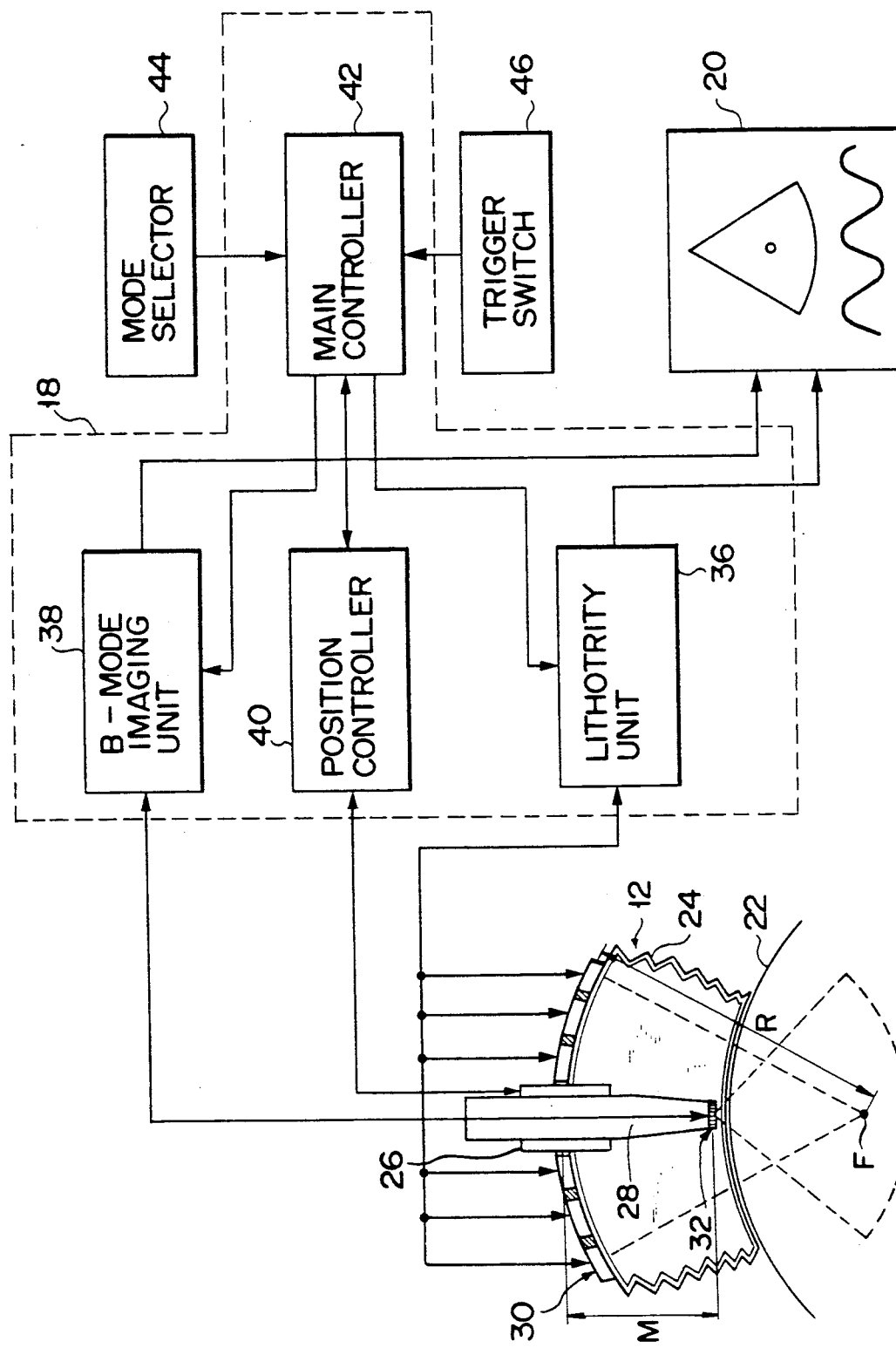
F I G. 2

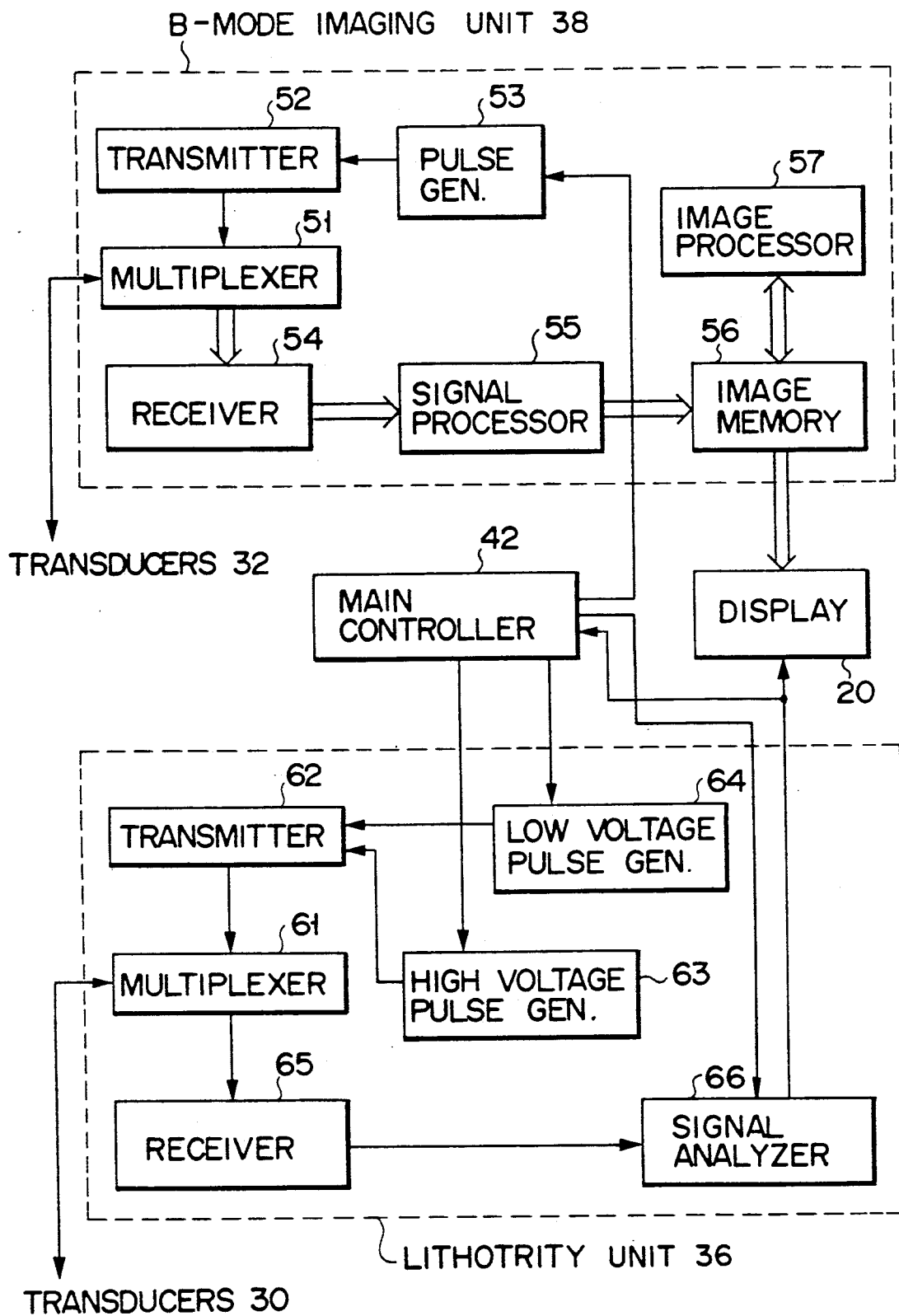
F I G. 3

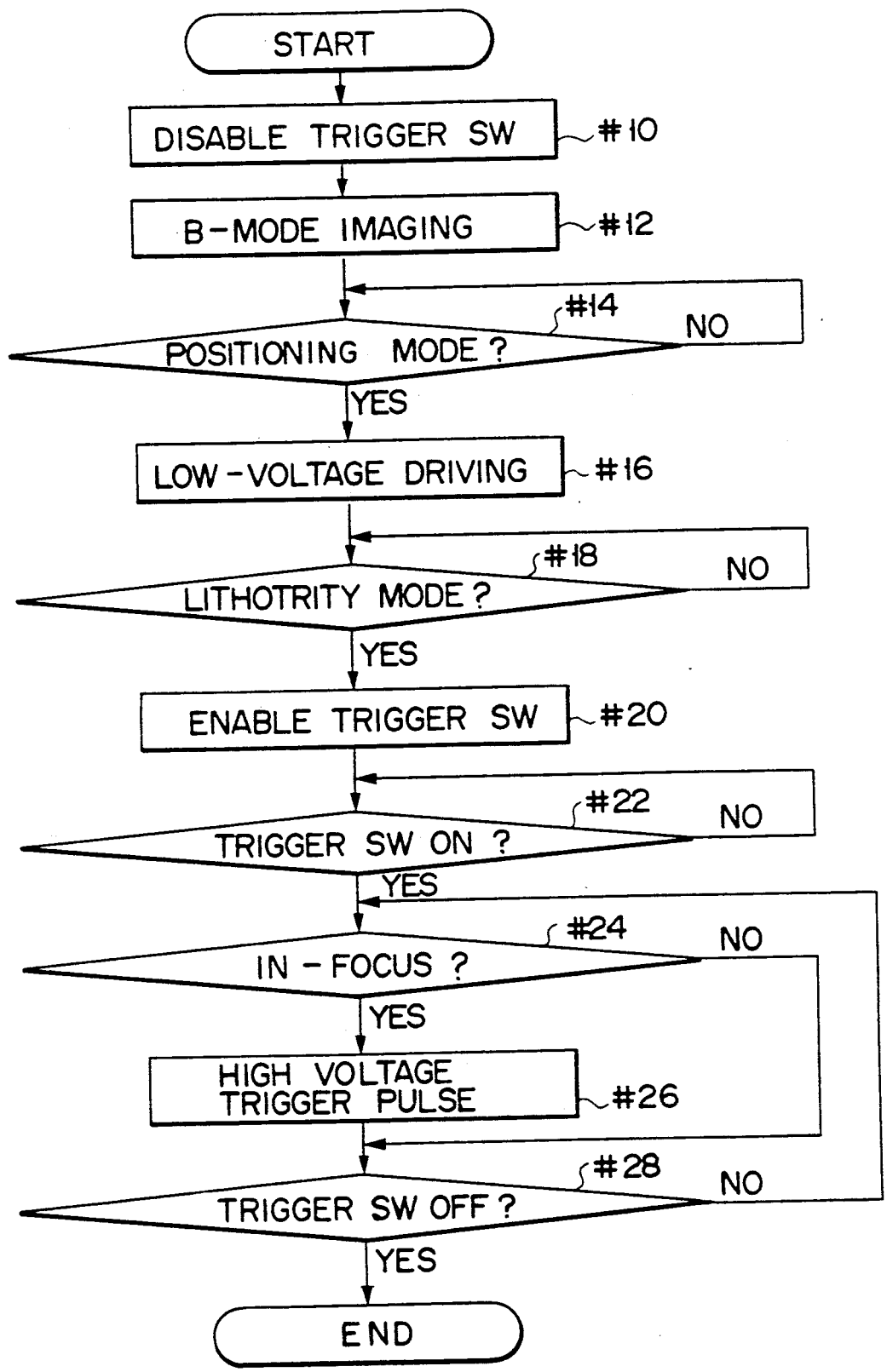
F I G. 4

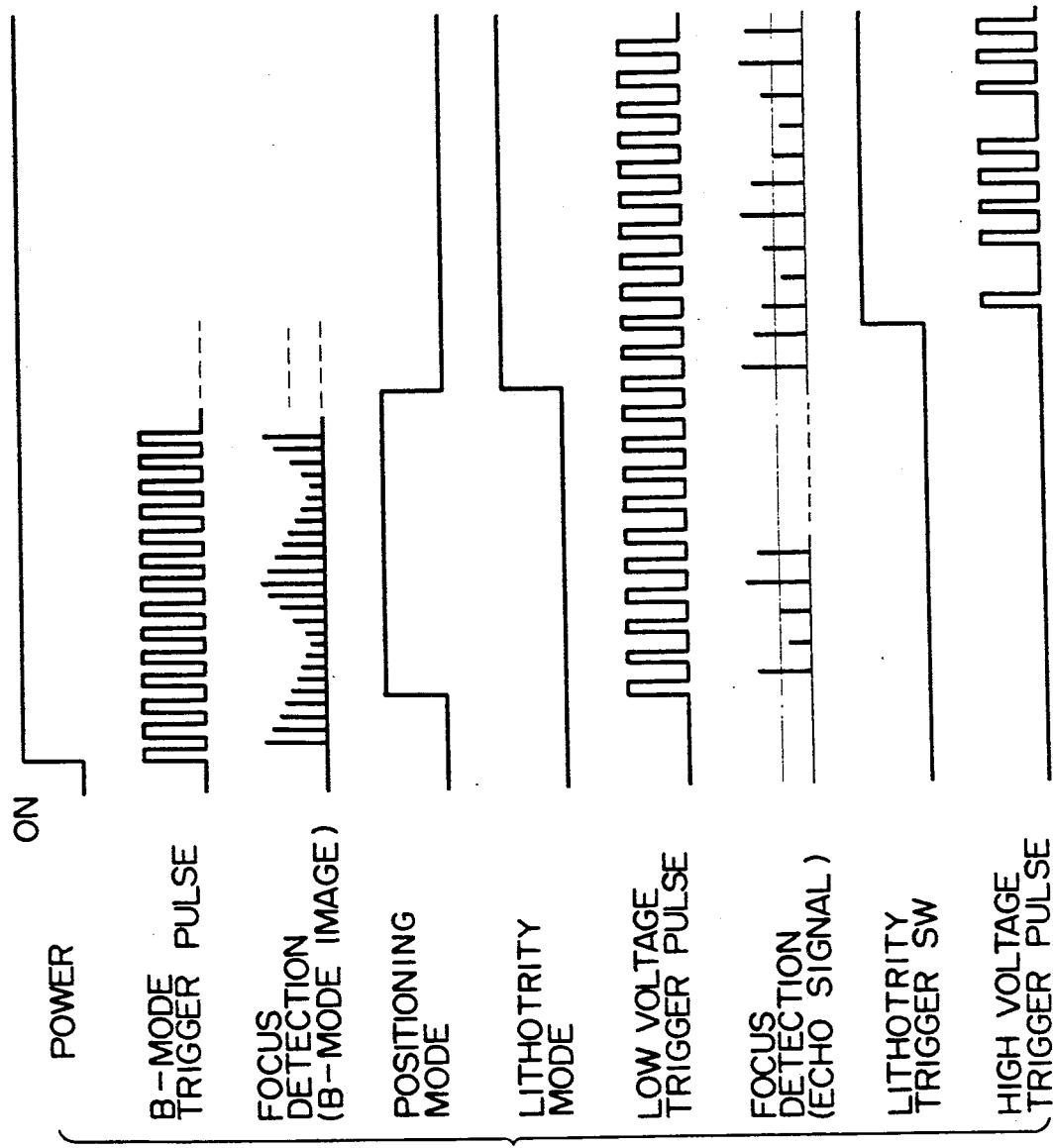
F I G. 5

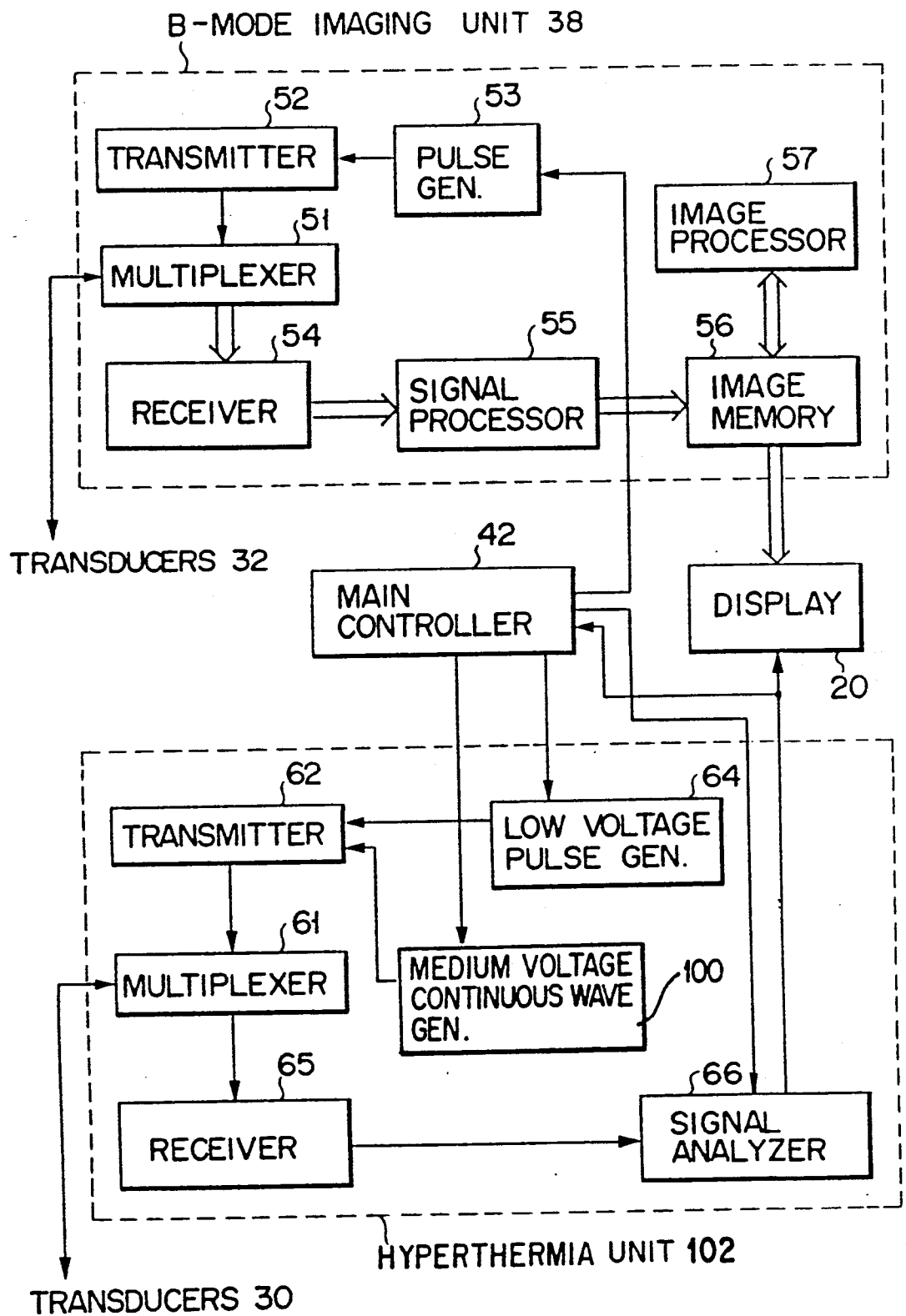
F I G. 7

LITHOTRITY APPARATUS USING ULTRASONIC WAVES OR SHOCK WAVES FOR PREVENTING ERRONEOUS IRRADIATION OF ULTRASONIC WAVES OR SHOCK WAVES

BACKGROUND OF THE INVENTION

1. Field of the Invention

The present invention relates to a treatment apparatus that converges energy waves, such as ultrasonic waves or shock waves, at one point to treat an object body to be treated (hereinafter referred to as a target section) in the noncontact state.

2. Description of the Related Art

A shock wave lithotrity apparatus is one of such apparatuses. In this apparatus, a piezoelectric transducer is driven by a high voltage pulse signal to converge high energy ultrasonic waves from this transducer at one point so as to generate a shock wave. Then, this shock wave is used to disintegrate a calculus, a cancer cell, etc.

An ultrasonic wave pulse apparatus disclosed in U.S. Pat. No. 4,617,931 (Dory) is a conventional example of the shock wave lithotrity apparatus. In this prior art, besides a shock wave generating transducer, an auxiliary transducer for echography is also installed. The shock wave generating transducer is not driven until the focus of the transducer is adjusted on the target section and it is confirmed that the target section coincides with the focus of the transducer using echography.

However, in this apparatus described above, in a case where an operator erroneously operates the switch for generating a shock wave during positioning even when the focus is not properly on the target section, the transducer would be driven so that a generated shock wave could be directed to areas other than the target section. In other words, according to the prior art, pressing the shock wave generating switch always activates and drives the piezoelectric transducer at a high voltage.

Instead of an ultrasonic wave, a discharge in water or an explosive is also used for generating a shock wave.

A hyperthermia apparatus, another treatment apparatus that uses ultrasonic waves, also has a similar problem. The hyperthermia apparatus could use, rather than a high voltage pulse signal, a medium voltage continuous wave signal to activate the transducer.

SUMMARY OF THE INVENTION

Accordingly, it is an object of the present invention to provide a noncontact type treatment apparatus which irradiates energy waves which are to be converged at one point to treat a target section using the energy waves in a noncontact state and prevents erroneous irradiation of the energy waves to start treating the target section even when positioning the converging point of the energy waves on the target section is not completed.

The noncontact type treatment apparatus according to this invention comprises an energy source for generating energy waves which converge at a given point, a treatment unit for driving the energy source at a high voltage to generate the energy waves in response to operation of an operating member to thereby treat an object at the converging point, and a mode selector for setting the operation mode of the treatment unit to a first mode for driving the energy source at a high voltage in response to the operation of the operating member or a second mode for inhibiting a high-voltage driving even upon operation of the operating member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 2 is a block diagram illustrating a control circuit of the first embodiment;

FIG. 3 is a detailed block diagram of a B-mode imaging unit and a lithotrity unit in the control circuit of FIG. 2;

FIG. 4 is a flowchart illustrating the operation of the first embodiment;

FIG. 5 is a timing chart illustrating the operation of the first embodiment; FIG. 7 shows another embodiment of a hyperthermia apparatus according to the present invention.

DETAILED DESCRIPTION OF THE PREFERRED EMBODIMENTS

Figure 1:
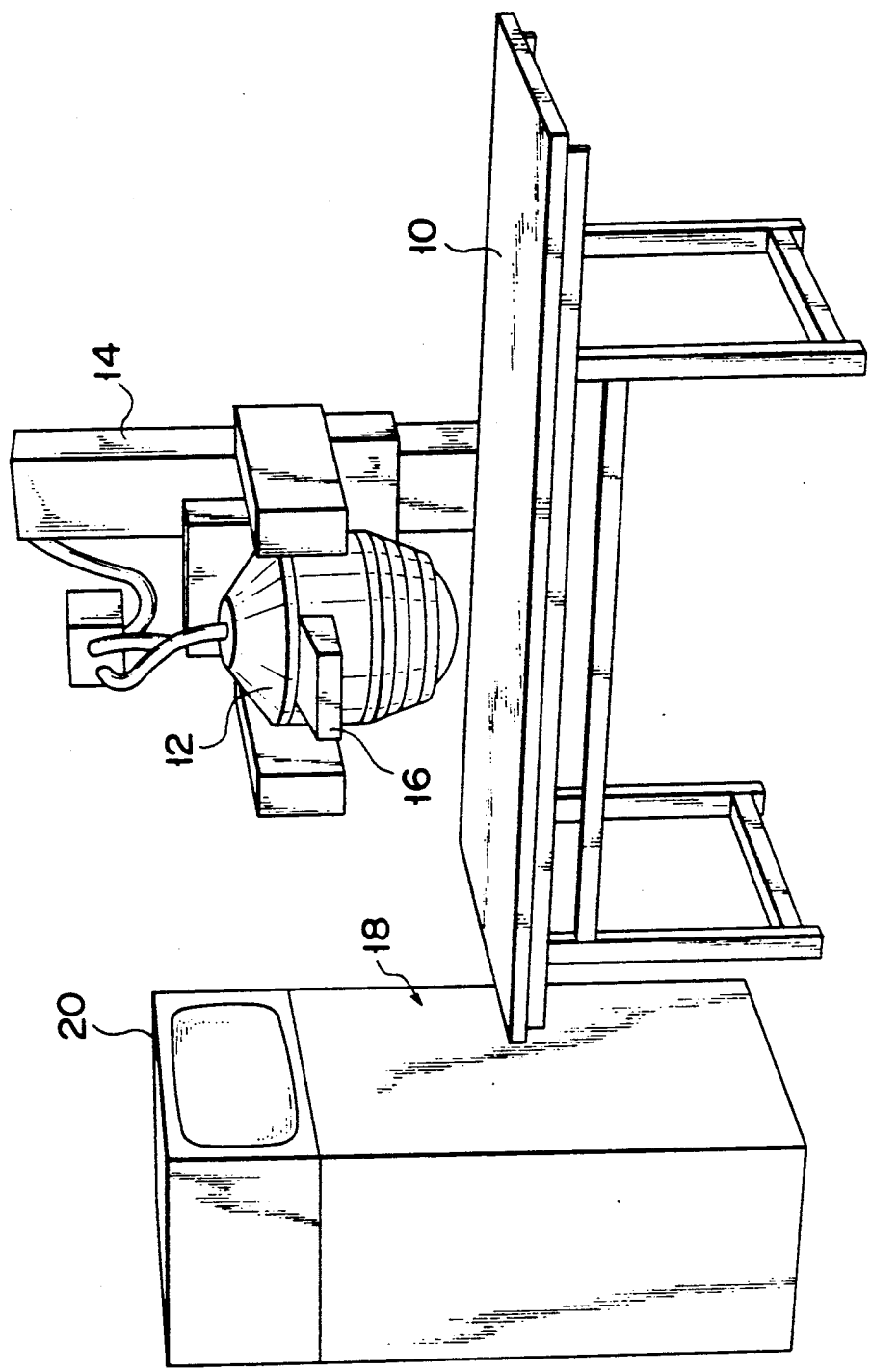
FIG. 1 is a perspective view of a shock wave treatment apparatus using ultrasonic waves, as the first embodiment of an noncontact type treatment apparatus according to this invention.

Preferred embodiments of a noncontact type treatment apparatus according to this invention will now be described with reference to the accompanying drawings. A description will be given of a treatment apparatus using a shock wave. FIG. 1 is a perspective view illustrating the outline of the first embodiment. Above a bed 10 where a patient (not shown) lies, an applicator 12 is supported by a supporting arm 14 in such a way that it can move in every direction over the patient. Also, it can be tilted around the vertical normal to the patient by a motor (not shown). The applicator 12 is also moved by a motor (not shown) and is positioned at a suitable location with respect to the patient. As will be described later, the applicator 12 comprises ultrasonic transducers which irradiate the ultrasonic waves for treatment, and a water bag which contains water as a medium to transmit the ultrasonic waves from the transducers to the patient.

An operation panel 16 for giving various instructions is provided in front of the applicator 12. The operation panel 16 includes switches, dials, and keys to input an instruction for movement and rotation of the applicator 12, an instruction for water supply/discharging, an instruction for starting a treatment and various operating parameters. A control unit 18 for performing the whole control is located by the bed 10. A display section 20 is mounted on the top of the control unit 18.

FIG. 2 is a block diagram of the control unit 18. The control unit 18 includes a lithotrity unit 36, a B-mode imaging unit 38, a position controller 40, and a main controller 42 to be connected to the units 36 and 38 and the controller 40. The applicator 12, which is also connected to the units 36 and 38 and the controller 40, comprises a water bag 24 having its top surface made of a curved rigid member, its bottom formed of a flexible film, and its side having a bellows shape. That curved face has such a predetermined curvature that the focus F is set at a specific position on the center axis. A first transducer group 30 is attached on the water bag 24. The transducer group 30 has a number of piezoelectric transducers arranged in a predetermined pattern, which serve to generate ultrasonic waves to be converged on the focus F.

The water bag 24 is filled with water as an ultrasonic wave propagation medium, and its bottom touches a body surface 22 of the patient. The amount of water filled in the bag 24 can be changed by stretching/shrinking of the bellows. The propagation medium is not limited to water but other type may be used as well. The ultrasonic waves converged at the focus F are converted into a shock wave, which is used to disintegrate the target section, such as a calculus and a cancer cell at the position F. The distance between the transducer group 30 and the focus F is always the same. When it is found that a calculus does not coincides with the focus F while viewing a B-mode echography (to be described later), the focus F should be aligned with the calculus by altering the amount of water in the bag 24 by means of pump (not shown) or the like to stretch or shrink the bellows and thus to adjust the distance between the transducer group 30 and the patient's body surface 22.

The water bag 24 has a hole in the center of the upper surface. A rod probe 28 for acquiring an echography for the positioning is inserted in the hole in water-tight manner through a sliding mechanism 26, which includes a motor and an encoder. At the tip of the rod probe 28, a second transducer group 32 having a number of transducers for acquiring a B-mode echography, is disposed. A convex system or sector system or other system can be used as a scanning system of the transducer group 32. Further, mechanical scanning or electrical scanning may be used as well. The following description will be given with reference to a case where the electric sector scanning system is used. The diameter of the first transducer group 30 should be relatively large due to a large energy needed for the treatment. The diameter of the second transducer group 32 is required to be significantly smaller to avoid interfering the transferring of the ultrasonic waves from the first transducer group 30 for treatment. The probe 28 may be moved up and down with the sliding mechanism 26, based on an instruction from the operation panel 16. This function can always provide an echography at the proximity of the focus F, even if the bellows of the water bag 24 are stretched or shrunk. Also, a marker for indicating the position of the focus F is displayed on the echography according to the distance between the first transducer group 30 and the second transducer group 32. If a calculus is difficult to view, the applicator 12 may be rotated around the axis normal to the patient to change the slice in which an echography will be acquired.

The lithotrity unit 36 is connected to the first transducer group 30, the B-mode imaging unit 38 is connected to the second transducers 32, and the position controller is connected to the sliding mechanism 26. The position controller 40 drives the sliding mechanism 26 to control the rod probe 28 to position the target body in the center of the echography in response to the instructions from the operation panel 16. Outputs from the lithotrity unit 36 and from the B-mode imaging unit 38 are supplied to the display section 20. The main controller 42 is connected with a positioning/treatment mode selector 44, and a treatment trigger switch 46 which gives an instruction to generate an ultrasonic wave for treatment. The mode selector 44 and the trigger switch 46 may be either installed in the operation panel 16 or constituted by a foot switch.

FIG. 3 shows a detailed block diagram of the B-mode imaging unit 38 and the lithotrity unit 36. The B-mode imaging unit 38 performs electrical sector-scanning of the applicator 12, especially the second transducer group 32 at the tip of the probe 28, to provide an fan-shaped echography in order to position the focus F of the ultrasonic waves from the first transducer group 30 near the target section.

The B-mode imaging unit 38 includes a multiplexer 51 for switching between transmission and reception of the transducer group 32, a transmitter 52, a pulse generator 53 which produces a low voltage pulse signal (e.g., 100 V, 7.3 KHz) to send the ultrasonic waves from the transducer group 32 at a constant cycle for acquiring a B-mode echography, a receiver 54 for receiving an echo signal of the ultrasonic wave, a signal processor 55 for subjecting a received signal to luminance modulation for acquiring an echography, an image memory 56 which stores the echography information generated from the signal processor 55, and an image processor 57 for calculating the brightness of the image around the marker of the echography information stored in the image memory 56 to obtain the degree of focus-calculus matching that will be described later. Ultrasonic reflecting objects, such as calculus and bones, in the echography can increase the brightness of the image.

The lithotrity unit 36 drives the first transducer group 30 at the top of the water bag 24 with a high voltage pulse signal, to converge the high energy ultrasonic waves on the focus F. The ultrasonic waves are converted into a shock wave due to a non-linear mutual operation between the ultrasonic waves and the medium for transmitting the ultrasonic waves. The shock wave disintegrates a calculus. The lithotrity unit 36 also drives the first transducer group 30 by a low voltage pulse signal, irradiates a low energy ultrasonic wave on the target section, and receives echo information, such as the waveform of an envelope of the echo signal. In other words, the lithotrity unit 36 drives the transducer group 30 not only for the lithotrity operation, but also for an A-mode operation in which the intensity of the echo signal from a calculus is measured. The intensity in the A-mode operation indicates whether there is an ultrasonic reflecting object (calculus) at the focus F, i.e., it corresponds to the degree of focus-calculus matching. The lithotrity unit 36 comprises a multiplexer 61 for switching between transmission and reception of the first transducer group 30, a transmitter 62, a high voltage pulse (4 KV, 500 KHz, for example) generator 63 for sending a high energy ultrasonic wave from the transducer group 30 for disintegration of a calculus, a low voltage pulse generator 64 (50 V, 500 KHz, for example) for sending a low energy ultrasonic wave from the first transducer group 30 in order to get the A-mode information, a receiver 65 which receives an echo signal of the low energy ultrasonic wave, and a signal analyzer 66 which detects the envelope of the signal received through the receiver 65 to acquire the echo information.

Based on the signals from the mode selector 44 and the trigger switch 46, the main controller 42 sends a trigger pulse signal to the pulse generators 53, 63, and 64, so as to instruct the B-mode imaging unit 38 and the lithotrity unit 36 to send the ultrasonic waves.

The operation of the first embodiment will be described referring to the flowchart in FIG. 4. When the apparatus is powered on, and starts operating, the main controller 42 disables the trigger switch 46 from generating a shock wave in step #10. That is, it keeps the trigger switch 46 from being turned on even if it is switched, so that the high voltage pulse generator 63 never receives the high voltage pulse trigger, and the high energy ultrasonic waves can not be generated from the transducer group 30. Therefore, it is possible to prevent malfunction of the trigger switch 46, thereby preventing the normal parts of the patient from being disintegrated.

In step #12, the B-mode trigger pulse with the constant cycle (the frame cycle) starts to be supplied to the pulse generator 53, and the constant cycled ultrasonic waves are sent from the transducer group 32 for acquiring an echography. The echo signal of the ultrasonic wave enters the signal processor 55 so as to provide an echography. Then, the echography is displayed in the display section 20 while the power is on. The main controller 42 displays a marker on the focus F in the echography, based on the distance R between the geometrical center of the first transducer group 30 and the focus F and the distance M between the geometrical center of the first transducer group 30 and the second transducer group 32.

An operator operates the mode selector 44 for setting the positioning mode. The positioning mode can be automatically set after a predetermined period of time from start of operation. Then, if the setting of the positioning mode is detected in step #14, a predetermined low voltage trigger pulse starts to be supplied to the low voltage pulse generator 64, and a low energy ultrasonic wave is sent from the transducer group 30 for the A-mode operation in step #16. The echo signal of the low energy ultrasonic wave is input to the signal analyzer 66 through the multiplexer 61 and the receiver 65. The analyzer 66 detects the envelope of the echo signal and measures the intensity (peak value) of the echo signal. Through this process, it is possible to obtain the degree of focus-calculus matching. A chart of the degree of focus-calculus matching with regard to time is displayed together with the echography on the display section 20. While the apparatus is powered on, the first transducer group 30 is driven for the A-mode operation, and the chart showing the degree of focus-calculus matching is displayed. It is possible to display the degree of focus-calculus matching based on the output from the image processor 57.

Referring to the echography, the marker, and the chart of degree of focus-calculus matching, an operator adjusts the positions of the applicator 12 and the rod probe 28 for focusing the target section such as calculus on the point F.

After focusing, the operator selects a treatment mode with the mode selector 44. When the setting of the treatment mode is detected in step #18, the operation of the trigger switch 46 is permitted for generating a shock wave in step #20. In other words, as long as the focus is adjusted and the lithotrity mode is selected, the shock wave can be driven anytime with the trigger switch 46 on. This process requires not only to turn on the trigger switch 46, but also to select the mode for lithotrity before generating the shock wave. Then, errors of treating normal parts by erroneously operating the trigger switch 46 can be eliminated. In the treatment mode the position of the applicator 12 is fixed.

The trigger switch 46 is turned on in step #22. In step #24, it is determined whether the degree of focus-calculus matching is above the predetermined level or not, which is based on the intensity of the echo signal measured from the envelop information. When the matching degree is over the predetermined level, one high voltage trigger pulse is supplied to the high voltage pulse generator 63, and the transducer group 30 generates high energy ultrasonic waves in step #26. These ultrasonic waves, which are converged on the point F and are converted to a shock wave, are used to disintegrate the target body at the point F, such as a calculus. Therefore, even if the trigger switch 46 is on, a shock wave is not generated without certain conditions being met in that it is generated only when the focus-calculus correspondence rate is above the predetermined rate, thus improving the treatment safety. When confirming that the disintegration is completed through the echography, the operator sets off the trigger switch 46. On the other hand, when the disintegration is incomplete, the switch 46 is kept on.

In step #28, it is determined whether or not the trigger switch 46 is off. If it is detected in step #24 that the matching degree is not above the predetermined level, i.e., it is determined that the calculus is not located at the focus point F, the step #26 for generating a shock wave is skipped, and the discrimination step #28 is immediately executed after step #24. When it is detected that the switch 46 is turned on in turned off in step #28, the operation is terminated. When it is detected that the switch 46 is turned on in step #28 the flow returns to step #24 for determination of the matching degree.

FIG. 5 illustrates a timing chart of the above-mentioned operation. First the power is on, the main controller 42 always supplies the B-mode trigger pulse signal to the pulse generator 53. Then, the degree of calculus-focus matching is detected for each frame based on the brightness of the region around the calculus from an echography. The positioning mode is then selected, and the main controller 42 starts sending a low voltage trigger pulse to the pulse generator 64. Then, the calculus-focus matching degree is again detected in accordance with the envelope information of the received echo signal. Finally, in positioning mode, the trigger switch 46 is inhibited from being turned on. In the lithotrity mode, the main controller 42 supplies a high voltage trigger pulse to the pulse generator 63, as long as the trigger switch 46 is on and the calculus-focus matching degree is above the predetermined level shown in FIG. 5 by an alternate long and short dash line.

As described above, in the first embodiment there is a positioning mode and a lithotrity mode as an operation mode. As the positioning mode disables the trigger switch 46 from being turned on to generate a shock wave, it is possible to prevent malfunction-oriented treatment of normal parts. Also, in the positioning mode, the transducer is activated by a low voltage for obtaining the A-mode information and the intensity of the echo signal is detected for the accurate positioning of the transducer. Besides, the lithotrity safety may be improved by generating a shock wave only when the target is in-focus in the lithotrity mode.

Figure 6:
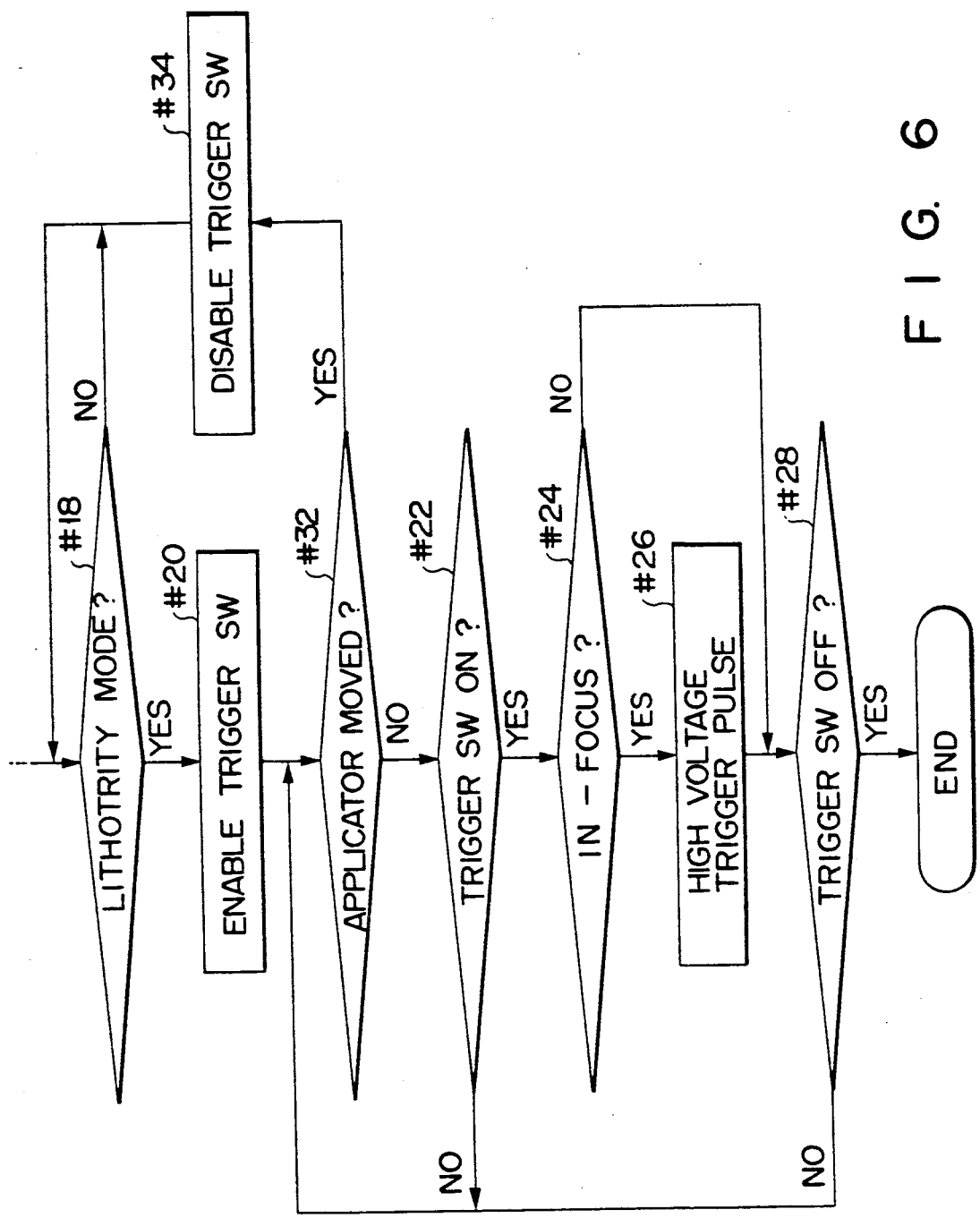
FIG. 6 is a flowchart illustrating the operation of the second embodiment.

The second embodiment will be now described. The detailed description of the block diagram of the control circuit is, however, omitted, for the second embodiment has the same structure as the first embodiment. FIG. 6 illustrates a flowchart of operation of the second embodiment. The same process as the first embodiment is taken in the positioning mode. The lithotrity mode is selected in step #18, and the trigger switch 46 is enabled for turning on in step #20 as per in the first embodiment.

Then, in the second embodiment, in step #32 it is determined whether any instruction to move the applicator 12 is input. The instruction includes a move instruction from the operation panel 16, as well as an instruction for the moving the bed 10. When it receives an instruction, the trigger switch 46 is disabled from being turned on in step #34, and the flow returns to step #18. Therefore, when the repositioning of the applicator 12 is necessary in the lithotrity mode, the positioning mode is automatically taken to prevent a shock wave from being generated. In fact, there are many opportunities that a calculus become off focus due to, for example, the patient's movement. The apparatus should often be repositioned in operation (moving the applicator 12 and the bed 10). The other area, besides the target body, will be disintegrated and will hurt the patient when the trigger switch is still on at that time. However, according to this embodiment, entering a positioning instruction enables the trigger switch 46 to be off, and the operation mode to return to the positioning mode. Therefore no accident as mentioned above would occur on the patient, and operations of the apparatus become less complicated.

When it is determined that no movement instruction is received in step #32, it is detected whether the trigger switch 46 is on in the step #22, as per the first embodiment. If it it detected that the degree of focus-calculus matching exceeds the predetermined level in step #24, one high voltage trigger pulse is generated to the pulse generator 63 in step #26. Then, the transducer group 30 irradiates a high energy ultrasonic waves, so that a shock wave is generated to be used to disintegrate a calculus.

As explained above, in the second embodiment, a movement instruction of the applicator automatically stops the lithotrity mode and shock wave generation, and changes the mode to the positioning mode. In other words, when resetting the applicator to focus on a calculus is necessary due to the patient's movement, the lithotrity mode is automatically set off according to a movement instruction of the applicator. Therefore, it is not necessary to turn off the trigger switch or to operate the mode selector, thus ensuring prompt lithotrity.

The foregoing description has been given with reference to a shock wave lithotrity apparatus that uses an ultrasonic wave. This invention can also be applied to a lithotrity apparatus using a shock wave which is generated by means of a discharge in water or an explosive. Besides, this invention can be applied to noncontact lithotrity apparatuses other than those that uses a shock wave; for example, this invention can be applied to a hyperthermia apparatus. The embodiment of this hyperthermia apparatus is shown in FIG. 7. This embodiment differs from the first embodiment shown in FIG. 3 only in that the lithotrity unit 36 is replaced by a hyperthermia unit 102 and the high voltage pulse generator 63 is replaced by a medium voltage continuous wave (e.g., 1 KV, 500 KHz) generator 100.

As explained above, according to this invention, a noncontact lithotrity apparatus focuses and irradiates energy waves on the target body for lithotrity. It has a positioning mode and a lithotrity mode as an operation mode to be selected by a selector. In the positioning mode, the energy wave for lithotrity is inhibited from being generated. Therefore, even if the target section is out of focus where the energy waves converge and a trigger switch is erroneously activated, it is possible to prevent treating the normal parts of the target body other than the target section. Also, in a case where resetting of the focus of the apparatus is required due to movement of the patient which renders the target section out of focus in the lithotrity mode, the operation mode automatically returns to the positioning mode when the resetting operation begins. Since it disables energy waves from being generated, it is necessary to perform only the focus resetting operation, and no mode selecting operation is required, thus providing excellent operability.

Additional advantages and modifications will readily occur to those skilled in the art. Therefore, the invention in its broader aspects is not limited to the specific details, representative devices (apparatuses), and illustrated examples (embodiments) shown and described herein. Accordingly, various modifications may be made without departing from the sprit or scope of the general inventive concept as defined by the appended claims and their equivalents.

What is claimed is:

1. A treatment apparatus using energy waves, comprising:
    energy wave generating means for generating energy waves and for converging the energy waves on a predetermined point of an object;
    means for selectively setting an operation mode of said energy wave generating means to one of a first mode and a second mode; and
    treating means having an operation member, for driving said energy wave generating means at a first level in response to an operation of said operation member to treat the object at the predetermined point when the operation mode of said energy wave generating means is set to said second mode, and for inhibiting said energy wave generating means from being driven at said first level, even upon the operation of said operation member, when said operation mode of said energy wave generating means has been set to said first mode.

2. The apparatus according to claim 1, further comprising:
    ultrasonic generating means for generating ultrasonic waves for scanning a predetermined plane of the object;
    means for obtaining an echography from an echo of said ultrasonic waves generated by said ultrasonic generating means;
    means for detecting an echo obtained from said energy waves generated by said energy wave generating means when said energy wave generating means is driven by a pulse signal having a second level, said second level being lower than said first level;
    display means for displaying an image of said echography and an output from said echo detecting means; and means for driving said echography obtaining means, said echo detecting means, and said display means when said operating mode of said energy wave generating means has been set to any of said first and second modes.

3. The apparatus according to claim 2, wherein said treating means comprises:
   means for detecting a brightness of a part of said displayed echography image which includes the predetermined point; and
   means for driving said energy wave generating means at said first level in response to the operation of said operation member only when said brightness detected by said brightness detecting means is larger than a predetermined brightness value and said operation mode of said energy wave generating means is set to said second mode.

4. The apparatus according to claim 2, wherein said treating means comprises means for driving said energy wave generating means at said first level in response to the operation of said operation member only when the output of said echo detecting means is larger than a predetermined echo value and said operation mode of said energy wave generating means is set to said second mode.

5. The apparatus according to claim 2, wherein said energy wave generating means comprises a first group of piezoelectric transducers arranged on a curved surface in a predetermined pattern, and said ultrasonic generating means comprises a second group of piezoelectric transducers arranged substantially at a center and in front of said first group of piezoelectric transducers.

6. The apparatus according to claim 2, wherein said echography obtaining means comprises means for displaying a marker on the displayed echography image to denote the predetermined point in accordance with a distance between said energy wave generating means and said ultrasonic generating means.

7. The apparatus according to claim 1, further comprising:
   means for adjusting a position of said energy wave generating means with respect to the object when said operation mode of said energy wave generating means is set to said first mode; and
   means for changing the operation mode of said energy wave generating means to the first mode when said adjusting means is to be operated and said operation mode of said energy wave generating means has been set to the second mode.

8. The apparatus according to claim 7, further comprising means for fixing the position of said energy wave generating means after the position has been adjusted by said adjusting means.

9. The apparatus according to claim 1, wherein said treating means comprises means for driving said energy wave generating means with a pulse signal having said first level to treat the object with a shock wave.

10. The apparatus according to claim 1, wherein said treating means comprises means for driving said energy wave generating means with a continuous wave signal having said first level to treat the object in a hyperthermia manner.

11. A treatment apparatus using energy waves, comprising:
    energy wave generating means for generating energy waves and for converging the energy waves on a predetermined point of an object;
    means for adjusting a position of said energy wave generating means with respect to the object;
    treating means having an operation member, for driving said energy wave generating means at a first level in response to an operation of said operation member to treat the object at the predetermined point; and
    means for inhibiting said energy wave generating means from being driven at said first level, even upon the operation of said operation member, when the adjusting means is to be operated.

12. The apparatus according to claim 11, further comprising means for selectively setting an operation mode of said apparatus to one of a first and a second mode, when the operation ode is set to the first mode said adjusting means is enabled and said treating means is disabled, and when the operation mode is set to the second mode the position of said energy wave generating means with respect to the object is fixed and said treating means is enabled.

13. The apparatus according to claim 12, further comprising:
    ultrasonic generating means for generating ultrasonic waves for scanning a predetermined plane of the object;
    means for obtaining an echography from an echo of said ultrasonic waves generated by said ultrasonic generating means;
    means for detecting an echo obtained from said energy waves generated by said energy wave generating means when said energy wave generating means is driven by a pulse signal having a second level, said second level being lower than said first level;
    display means for displaying an image of said echography and an output from said echo detecting means; and
    means for driving said echography obtaining means, said echo detecting means, and said display means when said operation mode of said energy wave generating means has been set to any of said first and second modes.

14. The apparatus according to claim 13, wherein said treating means comprises:
    means for detecting a brightness of a part of said displayed echography image which includes the predetermined point; and
    means for driving said energy wave generating means at said first level in response to the operation of said operation member only when said brightness detected by said brightness detecting means is larger than a predetermined brightness value and said operation mode of said energy wave generating means is set to said second mode.

15. The apparatus according to claim 13, wherein said treating means comprises means for driving said energy wave generating means at said first level in response to the operation of said operation member only when the output of said echo detecting means is larger than a predetermined echo value and said operation mode of said energy wave generating means is set to said second mode.

16. The apparatus according to claim 13, wherein said energy wave generating means comprises a first group of piezoelectric transducers arranged on a curved surface in a predetermined pattern, and said ultrasonic generating means comprises a second group of piezoelectric transducers arranged substantially at a center and in front of said first group of piezoelectric transducers.

17. The apparatus according to claim 13, wherein said echography obtaining means comprises means for displaying a marker on the displayed echography image to denote the predetermined point in accordance with a distance between said energy wave generating means and said ultrasonic generating means.

18. The apparatus according to claim 13, wherein said treating means comprises means for driving said energy wave generating means with a pulse signal having said first level to treat the object with a shock wave.

19. The apparatus according to claim 13, wherein said treating means comprises means for driving said energy wave generating means with a continuous wave signal having said first level to treat the object in a hyperthermia manner.

* * * * *

UNITED STATES PATENT AND TRADEMARK OFFICE
CERTIFICATE OF CORRECTION

PATENT NO. : 5,078,143
DATED : January 07, 1992
INVENTOR(S) : Kiyoshi Okazaki et al.

It is certified that error appears in the above-identified patent and that said Letters Patent is hereby corrected as shown below:

Claim 12, column 10, line 15, change "ode" to --mode--.

Signed and Sealed this

Twenty-second Day of June, 1993

Attest:

MICHAEL K. KIRK

*Attesting Officer*  *Acting Commissioner of Patents and Trademarks*